United States Patent
Zhang et al.

(10) Patent No.: US 8,842,411 B2
(45) Date of Patent: Sep. 23, 2014

(54) RF TRAPEZOIDAL CAPACITOR BASED EMI FEEDTHRU FILTER ASSEMBLY

(75) Inventors: Jin Zhang, Porter Ranch, CA (US); Wisit Lim, Santa Clarita, CA (US); Conor Flannery, Atlanta, GA (US)

(73) Assignee: Pacesetter, Inc., Sylmar, CA (US)

( * ) Notice: Subject to any disclaimer, the term of this patent is extended or adjusted under 35 U.S.C. 154(b) by 405 days.

(21) Appl. No.: 13/033,400

(22) Filed: Feb. 23, 2011

(65) Prior Publication Data

US 2012/0215288 A1  Aug. 23, 2012

(51) Int. Cl.
*H01G 4/30* (2006.01)
*A61N 1/37* (2006.01)
*A61N 1/375* (2006.01)
*H01G 4/35* (2006.01)

(52) U.S. Cl.
CPC ............... *H01G 4/35* (2013.01); *A61N 1/3718* (2013.01); *A61N 1/3754* (2013.01)
USPC ..................... 361/301.4; 361/306.2; 361/508; 361/509; 361/516; 361/517

(58) Field of Classification Search
USPC ................ 361/301.2, 301.4, 311, 313, 321.2, 361/321.4, 508–509, 516–519
See application file for complete search history.

(56) References Cited

U.S. PATENT DOCUMENTS

| | | | |
|---|---|---|---|
| 3,308,350 A | 3/1967 | Smyth et al. | |
| 4,205,364 A | 5/1980 | Pereira, Jr. | |
| 5,388,024 A | 2/1995 | Galvagni | |
| 5,650,759 A | 7/1997 | Hittman et al. | |
| 5,735,884 A | 4/1998 | Thompson et al. | |
| 5,745,335 A * | 4/1998 | Watt .............................. | 361/313 |
| 5,836,992 A | 11/1998 | Thompson et al. | |
| 5,896,267 A | 4/1999 | Hittman et al. | |
| 5,959,829 A | 9/1999 | Stevenson et al. | |
| 5,973,906 A | 10/1999 | Stevenson et al. | |
| 6,297,943 B1 | 10/2001 | Carson | |
| 6,349,025 B1 * | 2/2002 | Fraley et al. .................. | 361/302 |
| 6,459,935 B1 | 10/2002 | Piersma | |
| 7,035,076 B1 | 4/2006 | Stevenson | |
| 7,068,491 B1 | 6/2006 | Burdon et al. | |
| 7,199,995 B2 | 4/2007 | Stevenson | |
| 7,569,452 B2 | 8/2009 | Fu et al. | |
| 7,623,336 B2 | 11/2009 | Stevenson et al. | |
| 7,693,576 B1 * | 4/2010 | Lavie et al. ...................... | 607/37 |
| 7,804,676 B2 | 9/2010 | Brendel et al. | |
| 7,835,788 B1 | 11/2010 | Godau et al. | |
| 2005/0024837 A1 | 2/2005 | Youker et al. | |
| 2007/0053137 A1 | 3/2007 | Fu et al. | |
| 2007/0179551 A1 | 8/2007 | Iyer et al. | |
| 2008/0050649 A1 | 2/2008 | Goldstein et al. | |

FOREIGN PATENT DOCUMENTS

| | | |
|---|---|---|
| EP | 1760735 A1 | 3/2007 |
| EP | 1834666 A2 | 9/2007 |
| WO | 2007035443 A1 | 3/2007 |

* cited by examiner

*Primary Examiner* — Nguyen T Ha

(57) ABSTRACT

A multi-layer capacitor includes a first capacitor layer and a second capacitor layer adjacent and substantially parallel to the first capacitor layer. The second capacitor layer has a surface area that is less than the surface area of the first capacitor layer.

20 Claims, 10 Drawing Sheets

RF TRAPEZOIDAL CAPACITOR BASED EMI FEEDTHRU FILTER ASSEMBLY

CROSS-REFERENCE TO RELATED APPLICATIONS

This application is related to U.S. patent application Ser. No. 12/179,503, filed Jul. 24, 2008, titled "Implantable Pulse Generator EMI Filtered Feedthru Using Discrete Capacitors," the disclosure of which is herein incorporated by reference in its entirely.

FIELD OF THE INVENTION

The present invention relates generally to a trapezoidal capacitor and a trapezoidal capacitor based EMI feed through filter assembly.

BACKGROUND OF THE INVENTION

Compact, high voltage capacitors are utilized as energy storage reservoirs in many applications, including implantable medical devices. Implantable medical devices (IMDs) include implantable cardiac devices such as, for example, pacemakers, cardioverters and defibrillators. The term "implantable cardioverter defibrillator" or simply "ICD" is used herein to refer to any implantable cardiac device or implantable cardioverter defibrillator ("ICD").

ICDs are typically implanted in patients suffering from potentially lethal cardiac arrhythmias. Arrhythmia, meaning "without rhythm," denotes any variance from normal cardiac rhythm. Heartbeat irregularities are fairly common and many are harmless. A severe heartbeat irregularity known as ventricular tachycardia refers to a runaway heartbeat.

Fibrillation is an irregular rhythm of the heart caused by continuous, rapid, electrical impulses being emitted/discharged at multiple locations known as foci in the heart's atria and ventricles. Because a fibrillating heart is unable to properly pump blood through a patient's body, the longer a patient is in fibrillation, the greater the potential damage that can occur to the patient's heart. Thus, after the start of fibrillation, it is preferable to apply defibrillating therapy to the patient as soon as possible. An ICD is designed to apply such therapy automatically and quickly to minimize damage to the heart.

An ICD monitors cardiac activity and decides whether electrical therapy is required. For example, if a tachycardia is detected, pacing or cardioversion therapy may be used to terminate the arrhythmia. If fibrillation is detected, defibrillation is the only effective therapy. Both cardioversion and defibrillation require that a high voltage shock be delivered to the heart.

Typical ICDs include a set of electrical leads, which extend from a sealed housing into the walls of a heart after implantation. Within the housing are a battery for supplying power, a capacitor for delivering bursts of electric current through the leads to the heart, and monitoring circuitry for monitoring the heart and determining when, where, and what electrical therapy to apply. The monitoring circuitry generally includes a microprocessor and a memory that stores instructions not only dictating how the microprocessor controls delivery of therapy, but also controlling certain device maintenance functions, such as maintenance of the capacitors in the device. One example of an ICD is shown in U.S. Pat. No. 7,835,788, issued Nov. 16, 2010, the disclosure of which is incorporated herein in its entirety as though set forth in full below.

An implantable pulse generator feedthru is used for an electrical pathway extending between the electrically conductive lead securing components of a header of the pulse generator and the electrical components, such as an output flex, hybrid, etc., hermetically sealed in the housing or can of the pulse generator.

Feedthrus are mounted in the wall of the housing or can and include feedthru wires extending through the feedthrus. Feedthrus provide insulated passageways for feedthru wires, such as platinum iridium (Pt/Ir) wires, through the wall of the can. The header ends of the feedthru wires are electrically connected to connector blocks that mechanically and electrically couple with connector ends of implantable medical leads, and the can ends of the feedthru wires are electrically connected to the electrical components housed in the can of the pulse generator.

Feedthrus may include a filter element to filter out unwanted signals, such as electromagnetic interference ("EMI"). EMI feedthru filters used in ICDs require a high radio frequency (RF) performance, specifically a high voltage rating in a small feedthru housing assembly. The RF performances include high series resonant frequency (SRF), wide band width and high Q, etc.

In order to meet these specifications, not only the feedthru housing assembly needs to be optimized to accommodate the large valued capacitors, but also the large valued capacitors themselves need to be optimized.

In practice, RF capacitors used in an RF transceiver or RF decoupling circuit only have a value from about 0.5 pico Farads (pF) to several hundred pF. Capacitors used in feedthru filters will usually have a value range from about 1 to 5 nano-Farads, which is 10 times larger than regular RF capacitors.

Fundamentally these large valued capacitors (e.g., from 1-5 nF) are composed of multi-layer capacitors (MLC), wherein several single layer capacitors inside the capacitor body are vertically stacked and connected in parallel to make a larger valued capacitor. The larger the capacitance values that are required, the more single layer capacitors that need to be stacked.

In practice, a single layer capacitor contains some series parasitic inductance which will downgrade the RF performance. In particular, it will generate an SRF frequency point. At operating frequencies above the SRF, the capacitor will behave like an inductor and downgrade the RF performance of the capacitor.

When implementing a large valued MLC capacitor, the parasitic inductances accumulate when multiple single layer capacitors are stacked inside a multi-layer capacitor body.

A large valued capacitor will have more parasitic series inductance and generate a very low SRF frequency point. This will downgrade the RF performance of the capacitor. The larger the value of a capacitor, the higher the parasitic series inductance will be. In the worst case scenario, the SRF will be shifted to a very low frequency; this will cause the capacitor to work only at a low frequency band.

Several techniques, designs and processes have been developed to reduce the parasitic series inductance in a large valued RF capacitor. One such example is described in U.S. Pat. No. 7,623,336. These large valued RF capacitors are specially designed and implemented such that the SRF frequency can extend to very high frequency range. However, the costs of these custom made capacitors are significantly higher than standard capacitors.

SUMMARY OF THE INVENTION

A multi-layer capacitor includes a first capacitor layer and a second capacitor layer adjacent and substantially parallel to the first capacitor layer. The second capacitor layer has a surface area that is less than the surface area of the first capacitor layer.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated herein and form part of the specification, illustrate the present invention and, together with the description, further serve to explain the principles of the present invention and to enable a person skilled in the pertinent art to make and use the invention.

DETAILED DESCRIPTION OF THE INVENTION

Figure 1:
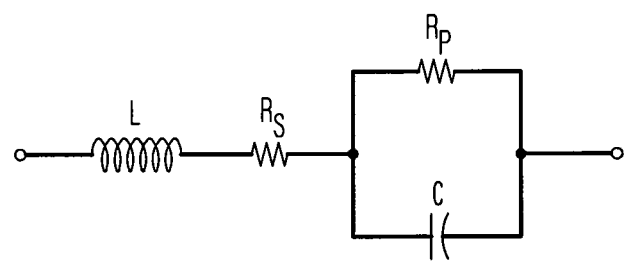
FIG. 1 shows a standard capacitor equivalent circuit model.

FIG. 1 shows a standard capacitor equivalent circuit model. In this model a parasitic series inductor L connects with a capacitor C to create a series LC resonant circuit. In addition, the LC resonant circuit includes a series resistance $R_s$ and a parallel resistance $R_p$.

Figure 2:
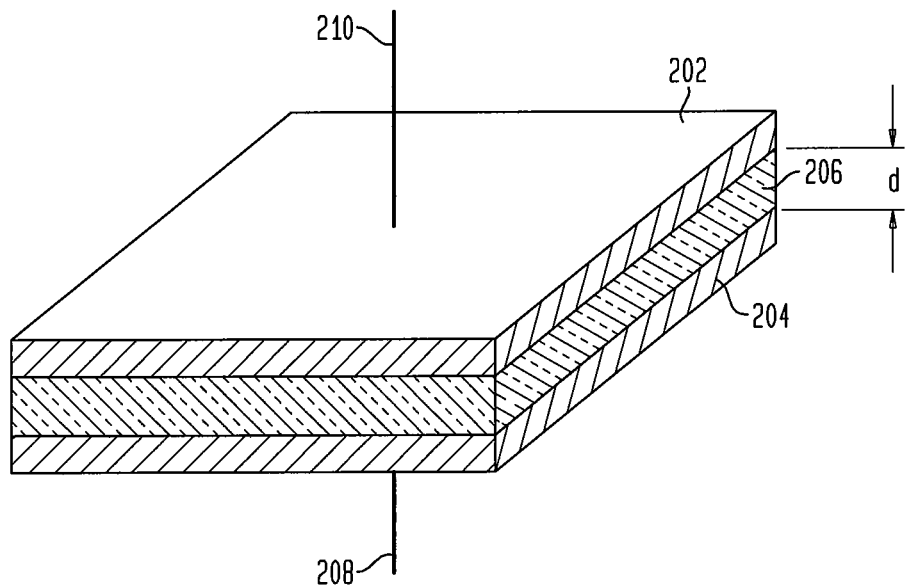
FIG. 2 shows a stylized view of a typical plate capacitor.

FIG. 2 shows a schematic representation of an embodiment of a single layer parallel plate capacitor. The capacitor comprises a first plate 202 and a second plate 204 separated by a dielectric 206. Plates 202 and 204 are connected to respective electrodes 208 and 210, which in turn are configured to be connected to other circuit elements in a well known manner.

Capacitance can be calculated if the geometry of the conductors and the dielectric properties of the insulator between the conductors are known. For example, the capacitance of a parallel-plate capacitor constructed of two parallel plates both of area A separated by a distance d is approximately equal to the following:

$$C = \varepsilon_r \varepsilon_0 \frac{A}{d},$$

where:
C is the capacitance;
A is the area of overlap of the two plates;
$\varepsilon_r$ is the relative static permittivity (sometimes called the dielectric constant) of the material between the plates (for a vacuum, $\varepsilon_r=1$);
$\varepsilon_0$ is the electric constant ($\varepsilon_0 \approx 8.854 \times 10^{-12}$ F m$^{-1}$); and
d is the separation between the plates.

Figure 3:
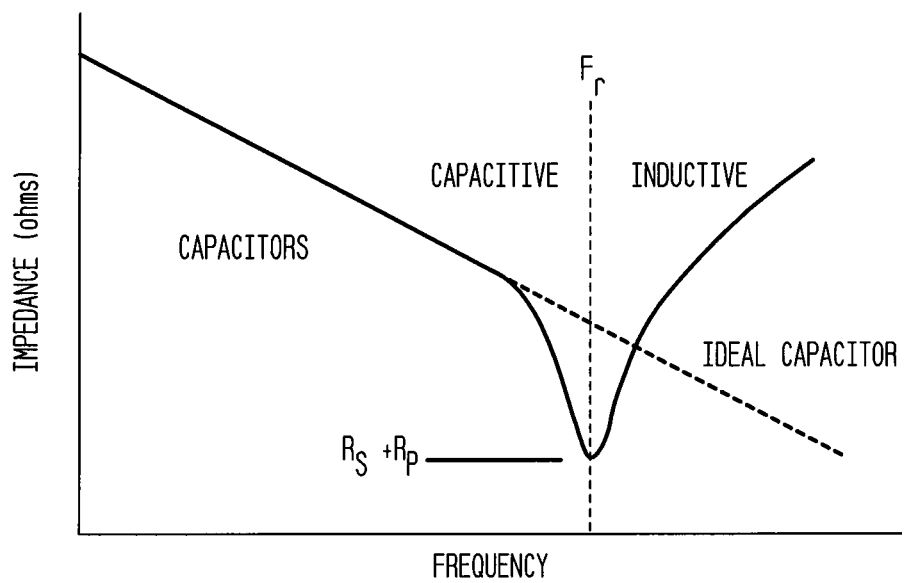
FIG. 3 shows a graph of the impedance characteristic vs. frequency for a practical and an ideal capacitor

FIG. 3 is a graph of impedance characteristics vs. frequency for an actual and an ideal capacitor. As can be seen, the impedance of an ideal capacitor decreases linearly with increasing frequency. In actual capacitors, on the other hand, the capacitance decreases sharply in a narrow frequency range until it reaches a minimum at the series resonant frequency (SRF). At frequencies greater than the SRF, the inductive impedance will increase so that above a certain frequency the capacitor will no longer function as a capacitor but will appear to be an inductor. This is due primarily to the parasitic inductances that are present in any capacitor, as will be described in more detail below.

As shown in FIG. 3, the series LC resonant circuit creates a peak which determines the series resonant frequency (SRF). A reduction in the inductance L will increase the SRF, which in turn improves the RF performance of the capacitor. At frequencies below the SRF, the capacitor behaves as a normal capacitor. However, at frequencies above the SRF, the capacitor will tend to behave like an inductor, and its RF performance will be degraded. Under the worst case, the capacitor will only work in the low frequency bands. It is desirable to have an SRF that is as high as possible, in order that the capacitor will behave as a capacitor at the highest frequencies possible.

Figure 4A:
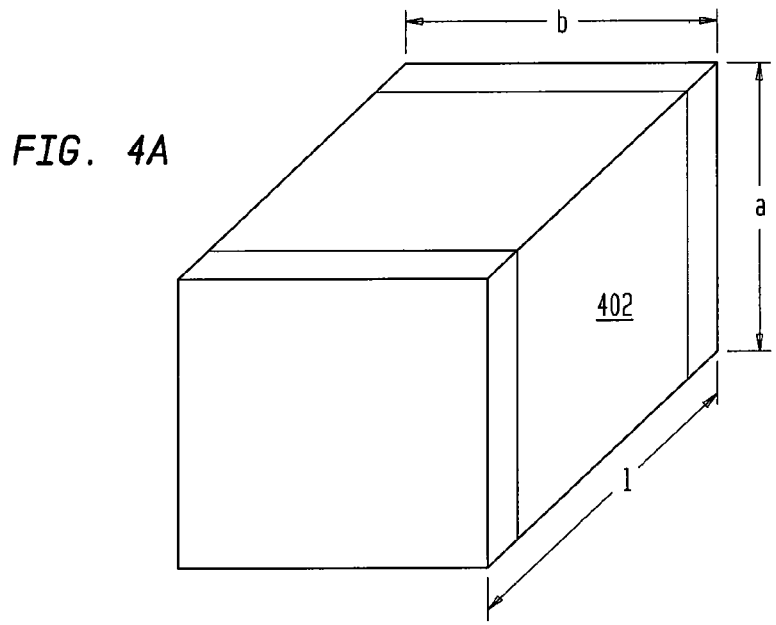
FIG. 4A shows a multi-layer cuboid capacitor
Figure 4B:
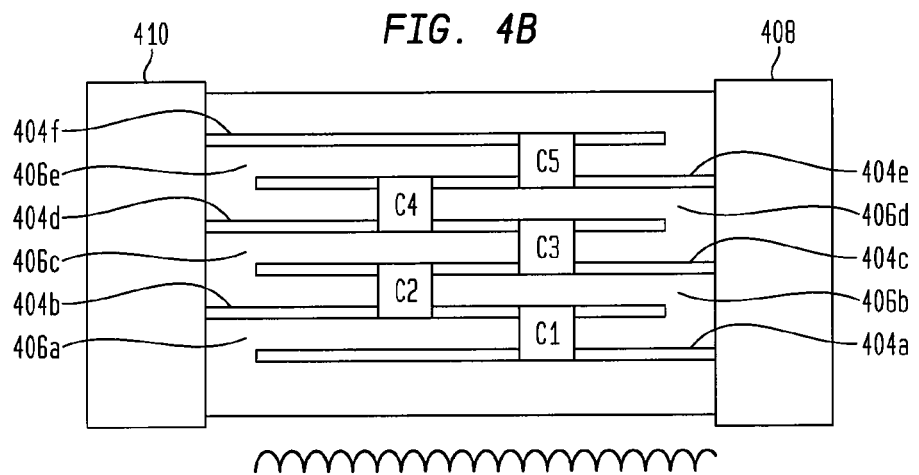
FIG. 4B shows s sectional view of a multi-layer cuboid capacitor.

Most capacitors today that are used in RF applications are multi-layer capacitors. A typical rectangular or cuboid multi-layer capacitor (MLC) is shown in FIGS. 4A and 4B. As used here, the term "cuboid" can mean a multi-layer capacitor having a square cross-section and a cubic or rectangular volume. FIG. 4A shows an MLC 402 that has a length "l", height "a", and width "b". FIG. 4B shows a cross-sectional view of an exemplary cuboid or rectangular MLC that comprises five capacitor layers, C1-C5. In this example, capacitor C1 comprises conductive plates 404a and 404b, separated by a dielectric layer 406a. Capacitor C2 comprises conductive plates 404b and 404c, separated by a dielectric layer 406b. Capacitor C3 comprises conductive plates 404c and 404d, separated by a dielectric layer 406c. Capacitor C4 comprises conductive plates 404d and 404e, separated by a dielectric layer 406d. Finally, capacitor C5 comprises conductive plates 404e and 404f, separated by a dielectric layer 406e. Capacitor plates 404a, 404c, and 404e are connected to a conductor 408. Capacitor plates 404b, 404d, and 404f are connected to a conductor 410. Conductors 408 and 410 are configured to be connected by respective leads to other circuit components in a known manner.

Figure 4C:
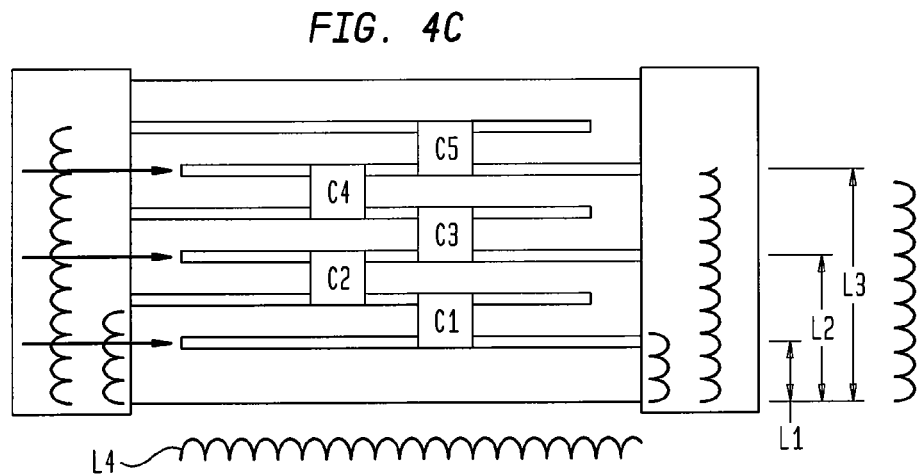
FIG. 4C shows a sectional view of a multi-layer capacitor with parasitic inductances

FIG. 4C shows the vertical and longitudinal parasitic inductances associated with a typical rectangular multi-layer capacitor. For example, vertical parasitic inductance L1 exists between capacitor C1 and ground, vertical parasitic inductance L2 exists between capacitor C3 and ground and vertical parasitic inductance L3 exists between capacitor C5 and ground. Corresponding vertical parasitic inductances exist with respect to capacitors C2 and C4, as well.

In addition to the vertical parasitic inductances, a longitudinal parasitic inductance L4 exists. This longitudinal parasitic inductance is a function of the length "l" of the capacitor. The longer the length of the capacitor, the larger the inductance value of L4. The longitudinal inductance is a distributive inductance.

The vertical inductances are created by the height of each different single capacitor layer; the higher the layer the higher the value of the vertical inductance. FIG. 4C illustrates, for example, that vertical parasitic inductance L3 capacitors C5 and ground is greater than the vertical parasitic inductance L1 between C1 and ground.

There is a tradeoff between the length of an RF capacitor and its voltage rating. If the length is reduced, the voltage rating is lowered. If the length is reduced too much, the voltage rating is lowered substantially. This may make the capacitor unsuitable for a specific application. On the other hand, increasing the length of the MLC causes an increase in the longitudinal parasitic inductance L4. This can result in a reduction of the SRF, thereby lowering the effective operating frequency of the MLC. If the vertical and longitudinal parasitic inductances associated with an MLC can be reduced while maintaining a high voltage rating, the SRF of the capacitor can be increased, thereby giving the capacitor a larger useful range.

Figure 5:
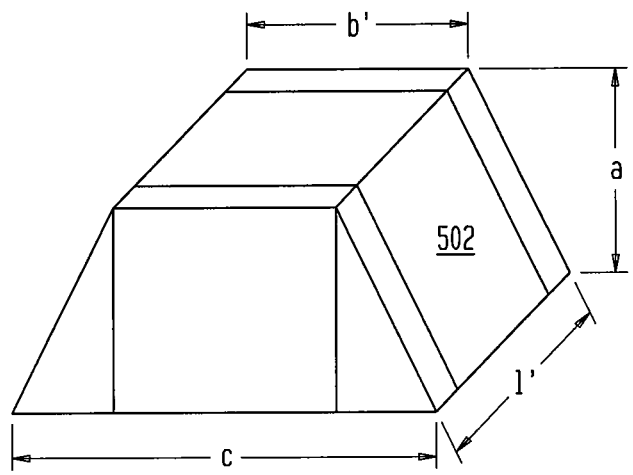
FIG. 5 shows a multi-layer trapezoidal capacitor according to an embodiment of the present invention.

Embodiments of the present invention accomplish this reduction in parasitic inductances by providing a trapezoidal shape to the multi-layer capacitor. A trapezoidal multi-layer capacitor of the type encompassed by the present invention is shown in FIG. 5. A capacitor 502 shown there has a length l', a height a, a base width c, and a top width b'. The trapezoidal capacitor 502 will have a larger cross-sectional area than a corresponding rectangular capacitor 402. In a rectangular capacitor each capacitor layer has the same area; thus each single capacitor layer will have the same value. By contrast, in a trapezoidal capacitor, the lower layers will have a larger capacitor area than the upper layers.

Figure 6A:
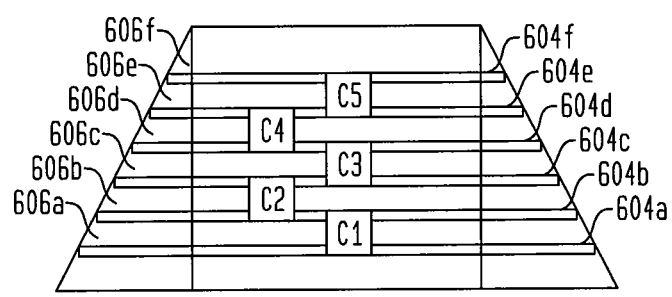
FIG. 6A shows a sectional view of a multi-layer trapezoidal capacitor
Figure 6B:
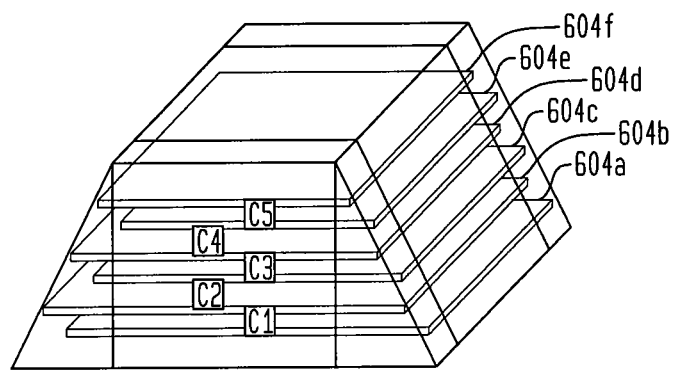
FIG. 6B shows a perspective view of a multi-layer trapezoidal capacitor.

FIGS. 6A and 6B respectively show sectional and perspective views of a trapezoidal MLC. Trapezoidal multi-layer capacitor 502 comprises, for example, a first capacitor C1 composed of plates 604a and 604b separated by a dielectric 606a, in which plate 604b has a smaller surface area than plate 604a; a second capacitor C2 composed of plates 604b and 604c separated by a dielectric 606b, in which plate 604c has a smaller surface area than plate 604b; a third capacitor C3 composed of plates 604c and 604d separated by a dielectric 606c, in which plate 604d has a smaller surface area than plate 604c; a fourth capacitor C4 composed of plates 604d and 604e separated by a dielectric 606d, in which plate 604e has a smaller surface area than plate 604d; and a fifth capacitor C5 composed of plates 604e and 604f separated by a dielectric 606e, in which plate 604f has a smaller surface area than plate 604e. It will be apparent to those skilled in the relevant art that any number of capacitor layers can be used, in which each succeeding plate has a smaller surface area than the preceding plate; and the invention is not limited to the embodiment shown in FIGS. 6A and 6B.

The capacitance value of a multi-layer capacitor is directly related to its volume, given the same voltage rating, dielectric material used and manufacturing techniques. Referring to the representative cuboid and trapezoidal capacitors 402 and 502, shown in FIGS. 4A and 5, respectively, an example of the capacitance calculation based on the volume of a multi-layer capacitor is as follows:

$$a = b = b' = 55;$$

$$c = 99$$

Cross sectional area of trapezoidal capacitor=4235;

Volume of trapezoidal capacitor=4235×l'

Cross sectional area of rectangular capacitor=3025;

Volume of rectangular capacitor=3025×l

To implement the same capacitance value in both a rectangular capacitor and a trapezoidal capacitor structure, $$l' = 3025\, l/4235 = 70\%\, l$$

The above calculation demonstrates that a trapezoidal capacitor having the same capacitance value as a rectangular capacitor has a length that is about 30% less than that of the rectangular capacitor.

In the trapezoidal design of embodiments of the present invention, the length is reduced by about 30% compared to the length of a corresponding rectangular capacitor. This reduction will not adversely affect the voltage rating. On the other hand, the longitudinal inductance will also be reduced by 30% compared to that of a rectangular capacitor. This greatly improves the RF performance and improves the SRF frequency of the trapezoidal capacitor compared to a comparable rectangular capacitor.

Each capacitor layer inside a trapezoidal capacitor has a different area compared to every other layer. The bottom layer capacitor (e.g., C1 in FIG. 6A) will have larger surface area than the immediately adjacent upper layer capacitor. Hence it will have a larger capacitance than the adjacent upper layer capacitor (e.g., C2). From the bottommost layer (e.g., C1) to the uppermost layer (e.g., C5), the capacitance will decrease linearly.

In a trapezoidal capacitor, most of the capacitance value will be concentrated at the bottom layer. The lower capacitance layers will have less vertical inductance than the uppermost layers. As a result, the overall vertical inductance will be smaller than that in rectangular capacitors.

Based on the above analysis, since the length of a trapezoidal capacitor is less than that of a corresponding rectangular capacitor, the trapezoidal capacitor will have both a lower longitudinal parasitic inductance and a smaller vertical parasitic inductance compared to a comparable rectangular capacitor.

Reducing the total parasitic series inductance will result in an increase in the SRF. It should be appreciated that a higher SRF is an important specification for a feedthru capacitor application. A high SRF will have deeper attenuation at higher frequency bands.

Figure 7:
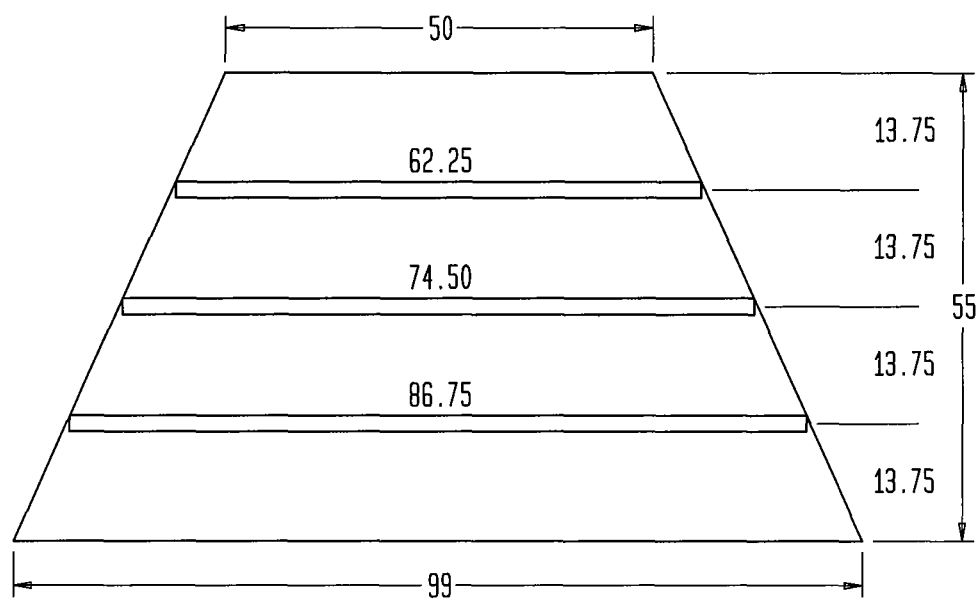
FIG. 7 depicts a simplified exemplary internal structure and dimensions of a three layer trapezoidal feedthru capacitor used to calculate vertical parasitic inductance.

FIG. 7 depicts a simplified exemplary internal structure and dimensions of a three layer trapezoidal feedthru capacitor used to calculate vertical parasitic inductance. FIG. 7 depicts three single layer capacitors inside a trapezoidal capacitor. The three layers have respective widthwise dimensions of 62.25, 74.5 and 86. The units are arbitrary. It should be understood that this structure and these dimensions are only exemplary and are not limiting of the scope of the invention.

An exemplary demonstrative calculation and estimate of the vertical parasitic inductance reduction in a trapezoidal capacitor compared to a comparable rectangular capacitor is shown below based on the exemplary dimensions shown in FIG. 7. The vertical inductance is directly related to the height of each layer of the capacitor.

The calculations below of vertical parasitic inductance are based on the sum of the product of height and width of each capacitor layer:

For a trapezoidal capacitor:

$$86.75 \times 13.75 + 74.5 \times 27.5 + 62.25 \times 41.25 = 5809$$

For a rectangular capacitor:

$$74.5 \times 13.75 + 74.5 \times 27.5 + 74.5 \times 41.25 = 6146$$

The trapezoidal capacitor will have 5809/6146=94.5% of the vertical inductance of a rectangular capacitor. Stated another way, there is a 5.5% reduction in vertical parasitic inductance in a trapezoidal capacitor compared to a comparable rectangular capacitor. Also, as noted above, a trapezoidal capacitor will have a length that is 70% of the length of a rectangular capacitor so that the longitudinal parasitic inductance is reduced by about 30%. The above calculation demonstrates that there is about 35.5% total series parasitic inductance reduction in a trapezoidal capacitor compared to a rectangular capacitor having the same capacitance value.

Figure 8:
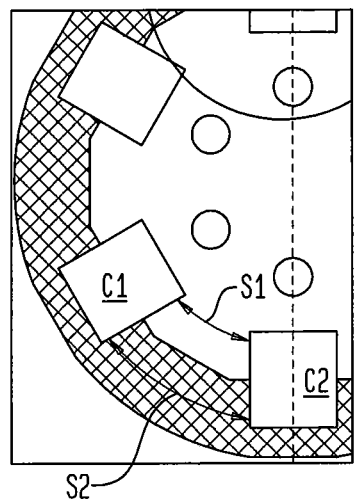
FIG. 8 shows a typical feed through assembly using cuboid multilayer capacitors.
Figure 9:
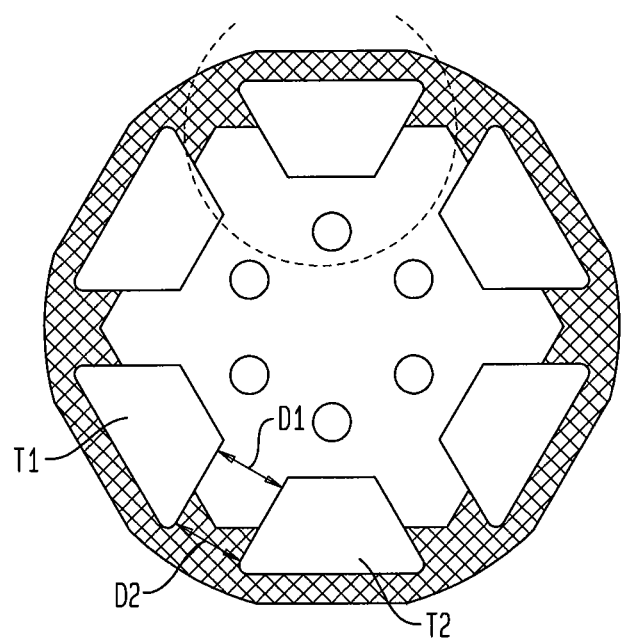
FIG. 9 shows a feed through assembly using trapazoidal capacitors according to embodiments of this invention

FIG. 9 shows a typical design of a six channel feedthru assembly using trapezoidal multilayer capacitors. FIG. 8 shows a relevant portion of an analogous six channel feedthru assembly using cuboid multilayer capacitors. In practice, there is an insulation (voltage rating) requirement in a multichannel feedthru assembly design that is the minimal distance requirement for neighbor channel capacitors.

In a cuboid MLC version of a feedthru assembly, the minimum separation S1 is located at the inner edge of two neighboring cuboid capacitors C1 and C2, while the maximum separation C2 between the two neighboring cuboid capacitors lies at external edges of the two cuboid capacitors. Thus the cuboid (square or rectangular) capacitor based feedthru structure does not efficiently utilize the available space of the feedthru housing assembly.

By contrast, in the feedthru assembly using trapezoidal MLCs, all the neighboring channel capacitors will have same separation between them. Thus, the separation distance D1 at the inner edge of neighboring trapezoidal capacitors T1 and T2 will be the same as the separation distance D2 at the outer edge of the neighboring trapezoidal capacitors. This will result in better space efficiency than the rectangular version. Due to a shorter length of the trapezoidal capacitor (70% as compared to the rectangular version), the feedthru assembly will have shorter length. A shorter feedthru assembly will also help to reduce the external grounding inductance.

Some examples of feedthru capacitor arrangements can be seen in U.S. Pat. No. 6,297,943, issued Oct. 2, 2001, and U.S. Pat. No. 7,693,576, issued Apr. 6, 2010, the disclosures of which are incorporated in their entirety as though set forth in full herein.

Figure 10:
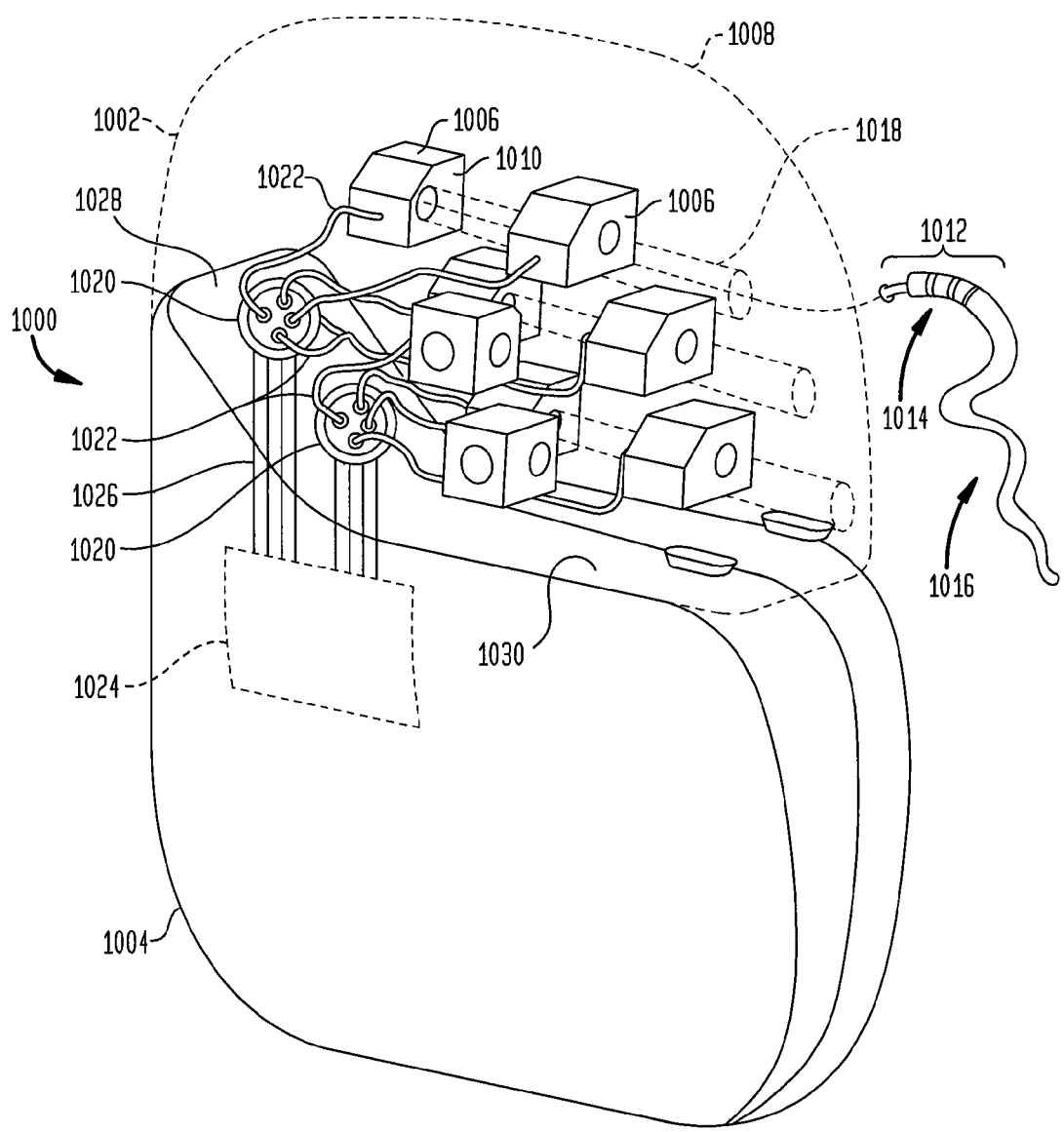
FIG. 10 shows an implantable pulse generator that utilizes an EMI filtered feedthru

Feedthrus are mounted in the wall of the housing or can of an IMD and include feedthru wires extending through the feedthrus. With reference to FIG. 10, an implantable pulse generator 1000 may utilize an EMI filtered feedthru having the trapezoidal capacitors described above. The pulse generator 1000 includes a header 1002 and a can or housing 1004. The header 1002 includes several connector blocks 1006 and a molded portion 1008 (shown in phantom) that encloses the blocks 1006. Each block 1006 includes an opening 1010 configured to receive therein and mate with a connector 1012 of a lead proximal end 1014, thereby forming an electrical connection between the connector block 1006 and the lead connector 1012 and mechanically securing the proximal end 1014 of a lead 1016 to the header 1002.

The header molded portion 1008 (shown in phantom) may be formed of a polymer material. Passages 1018 (shown in phantom) extend from the exterior of the molded portion 1008 to openings 1010 in the blocks 1006, providing a pathway for lead proximal ends 1012 to pass through the molded portion 1008 and enter the openings 1010.

The can 1004 includes feedthrus 1020 mounted in a wall of the can. Conductors 1022 (e.g., round wires, flat ribbon wires, flex cables or etc.) extend from the header sides of feedthrus 1020 to respective connector blocks 1006. The can 1004 provides a hermetically sealed enclosure for the pulse generator's electronic components 1024 (e.g., output flex, hybrid, or various other electronic components) housed within the can 1004. Conductors 1026 (e.g., round wires, flat ribbon wires, flex cables or etc.) extend from the can sides of feedthrus 1020 to electronic components 1024. Typically, the wall of the can 1004 is made of titanium or another biocompatible metal.

As shown in FIG. 10, in one embodiment, feedthrus 1020 are mounted in an inclined portion 1028 of the can 1004. In other embodiments, feedthrus 1020 may be mounted in a flat portion 1030 of the can 1004, or the feedthrus 1020 may be mounted in both the inclined and flat portions 1028, 1030 of the can 1004. In other embodiments, the feedthrus 1020 may also be mounted in the vertical side walls of the can 1004.

Figure 11:
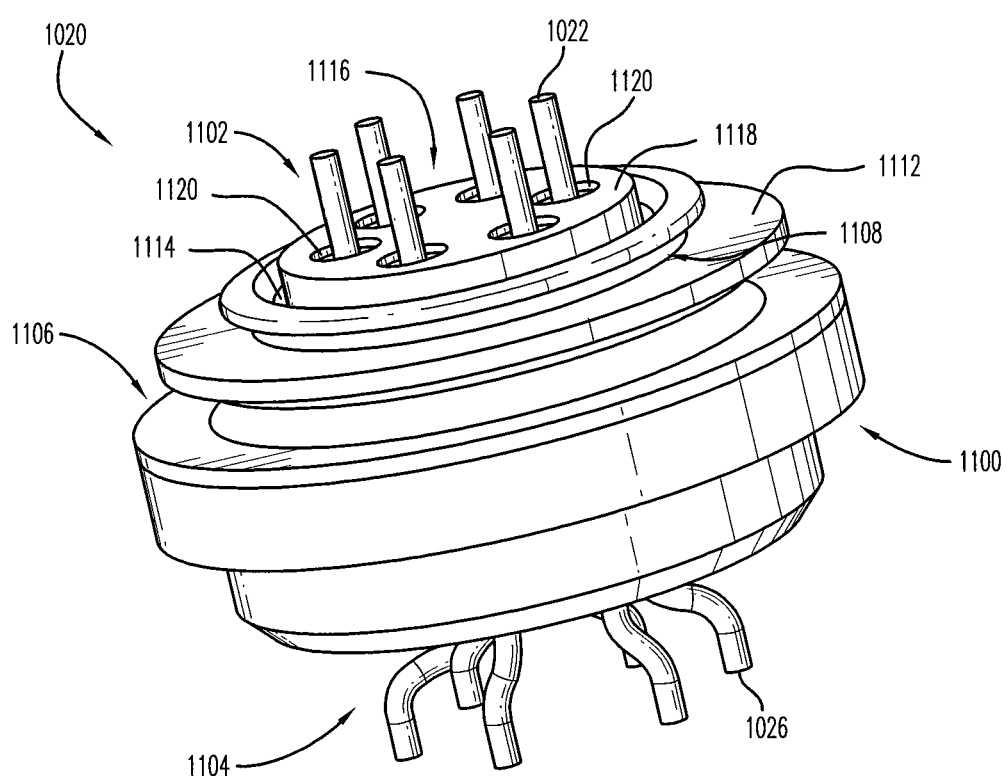
FIG. 11 shows a filter assembly of the type used in the implantable pulse generator of FIG. 10.
Figure 12:
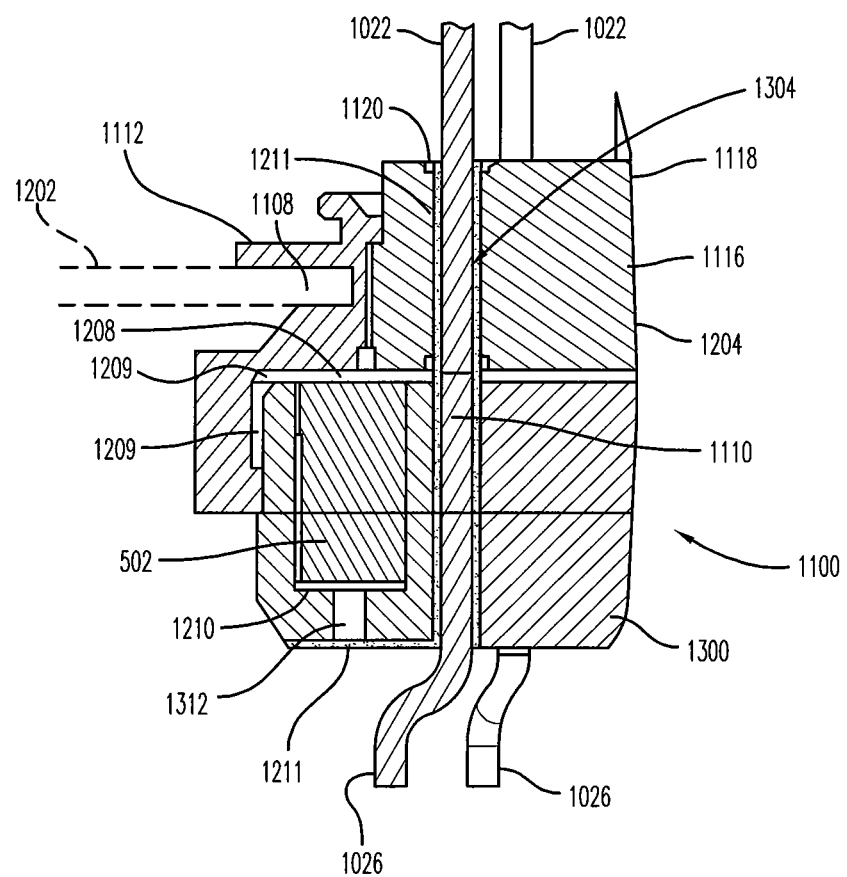
FIG. 12 shows a cutaway view of a portion of the filter assembly of FIG. 11.

As shown in FIG. 11, in one embodiment, a feedthru 1020 includes a header side 1102, a can side 1104, and a circular side 1106 that may vary in diameter such that it appears as a plurality of stacked rings with different diameters. A groove or slot 1108 may be defined by the varying diameter. As shown in FIG. 12, when a feedthru is assembled in a can, the groove or slot 1108 receives a wall 1202 of the can. Feedthru wires 1022/1026 extend between the header side 1102 and the can side 1104.

The outer circumference of a feedthru housing 1112 is defined by the groove or slot 1108 and circular side 1106. A central opening 1114 of the feedthru housing 1112 extends axially through the housing and may have a stepped construction. The central opening 1114 defines an aperture which is occupied by a core 1116.

In one embodiment, a feedthru 1020 includes six feedthru wires 1022/1026. The feedthru wires 1022/1026 may be Pt/Ir wires, such as 90% Pt/10% Ir wires. Electrical components 1024 in the can 1004 and the blocks 1006 in the header 1002 may be coupled to the wires 1022/1026 by soldering, brazing, welding or other suitable methods.

As can be understood from FIGS. 11 and 12, the core 1116 includes a first cylindrical portion 1118, a second cylindrical portion 1204 and feedthru wire openings 1120 extending longitudinally therethrough. The feedthru wires 1022/1026 (collectively 1110) extend through openings 1120, which provide an insulated passageway for wires through the core 1116 and, as a result, the feedthru 1020. The core 1116 may be ceramic, sapphire, or glass. The outer circumference of the core 1116 may be cylindrically stepped such that the first cylindrical portion 1118 has a smaller diameter than the second cylindrical portion 1204.

The core 1116 is received in the central opening 1114 of the housing 1112 such that the first cylindrical portion 1118 is exposed at the header side 1102 of the feedthru 1020 and the second cylindrical portion 1204 abuts a step 1206 in the central opening 1114 of the housing 1112.

Figure 13A:
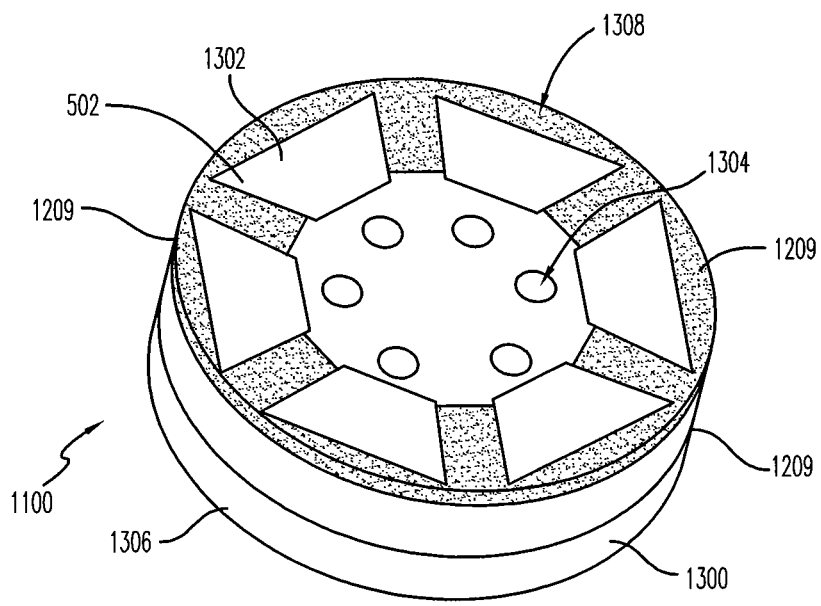
FIGS. 13A and 13B show two views of a feedthru of the type used in the filter assembly of FIG. 12.
Figure 13B:
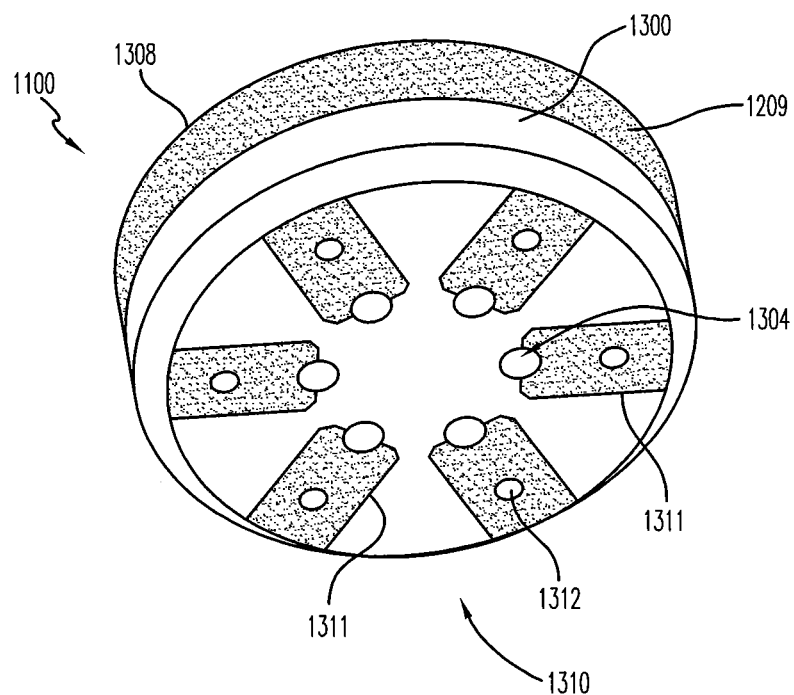

With reference to FIGS. 13A and 13B, the filter assembly 1100 includes a body 1300, cavities 1302, trapezoidal capacitors 502, feedthru wire openings 1304, an outer circumferential side 1306, a core side 1308 and an electronic interface side 1310. In one embodiment, there may be six, capacitor openings 1302. In other embodiments, there may be more than six chip capacitor openings or there may be less than six chip capacitor openings. The surfaces of the chip capacitor openings 1302 may be coated with an electrically conductive material, such as nickel, gold, platinum, etc. In one embodiment, the body 1300 of the filter assembly 1110 is a disc. In alternative embodiments, the body 1300 of the filter assembly 1110 may be a shape other than a disc, such as a hexagon or a rectangle. The filter assembly body 1300 may be formed of any electrically insulating material, such as ceramic, sapphire or glass that is brazable. The filter assembly body 1300 may be machined, molded or otherwise formed to fit the space and design constraints of the IMD.

The cavities 1302 are defined in the body 1300 of the filter assembly 1110 and open outwardly on the core side 1308 of the body 1300 to receive therein trapezoidal capacitors 502. In some embodiments (not shown), cavities 1302 may open outwardly on the electronic interface side 1310 of the body 1300 to receive therein trapezoidal capacitors 502. The cavities 1302 may be shaped to matingly receive the capacitors 502. The cavities 1302 have a bottom surface opposite their openings in the core side 1308 or opposite their openings in the electronic interface side 1310, as appropriate. In one embodiment, holes 1312 extend through the material of the body 1300 from the bottom surface of the cavities 1302 to form an opening in the electronic interface side 1310 of the body.

With reference to FIG. 12, the feedthru wire openings 1304 extend through the core 1116 and the filter assembly body 1300, providing a passageway for the feedthru wires 1110 to extend through and electrically connect to IMD components. The surfaces of the feedthru wire openings 1304 may be coated with an electrically conductive material, such as nickel, gold, platinum, etc.

The feedthru wire openings 1304 are arranged radially about a center point. In alternative embodiments, the openings 1304 may be arranged in a different pattern, e.g. not radially, or the openings 1304 may be located on an outside rim or edge. In one embodiment, there are six openings 1304. In alternative embodiments, there may be fewer than six openings 1304 or there may be more than six openings 1304.

With reference to FIG. 12, the trapezoidal capacitors 502 include a power end 1210 and a ground end 1208. The power end 1210 is electrically connected to the power trace 1211. The ground end 1208 is electrically connected to the ground trace 1209. In one embodiment, the minimum distance between opposite electrical potentials is approximately 0.03 inches.

As illustrated in FIG. 13A, the core side 1308 of the filter assembly body 1300 includes capacitor openings 1302, feedthru wire openings 1304 and ground traces 1209. The capacitor openings 1302 receive the trapezoidal capacitors 502. The trapezoidal capacitors 502 may be coupled to the openings 1302 by an electrically conductive epoxy or solder. As can be understood with reference to FIG. 10, the core side 1308 is electrically coupled to components in the header 1008 of the IMD via the feedthru wires 1022.

As illustrated in FIG. 13B, the electronic component interface side 1310 of the filter assembly body 1300 includes power traces 1311, feedthru wire openings 1304, and holes 1312 leading to the cavities 1302. As can be understood with reference to FIG. 10, the electronic component interface side 1310 is electrically coupled to the electrical components in the can 1004 of the IMD via the feedthru wires 1026.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all patents, patent applications and publications mentioned above are incorporated herein by reference.

What is claimed is:

1. An implantable medical device comprising a trapezoidal multi-layer thick film chip capacitor having a capacitance in the range of 1-5 nF, the capacitor comprising:
   a first capacitor layer; and
   a second capacitor layer adjacent and substantially parallel to the first capacitor layer and having a surface area that is less than the surface area of the first capacitor layer.

2. The implantable medical device of claim 1, further comprising:
   a third capacitor layer adjacent and substantially parallel to the second capacitor layer such that the second capacitor layer is disposed between the first and third capacitor layers, the surface area of the third capacitor layer being less than the surface area of the second capacitor layer.

3. The implantable medical device of claim 2, wherein said first, second and third capacitor layers together define a trapezoidal capacitor configuration.

4. The implantable medical device of claim 1, further comprising at least one additional capacitor layer that is substantially parallel to its immediately adjacent capacitor layer and has a surface area that is less than the surface area of the immediately adjacent capacitor layer.

5. The implantable medical device of claim 1, further comprising a plurality of additional capacitor layers, each additional capacitor layer being substantially parallel to its immediately adjacent preceding capacitor layer and having a surface area that is less than the surface area of the immediately adjacent preceding capacitor layer.

6. The implantable medical device of claim 5, wherein said first, second, and additional plurality of capacitor layers together define a trapezoidal capacitor configuration.

7. An EMI filtered feedthru for an implantable pulse generator, comprising:
   a filter assembly including a trapezoidal multi-layer thick film chip capacitor having a capacitance in the range of 1-5 nF, the capacitor having a first capacitor layer, and
   a second capacitor layer adjacent and substantially parallel to the first capacitor layer and having a surface area that is less than the surface area of the first capacitor layer; and
   a body including a cavity in which the capacitor resides.

8. The EMI filtered feedthru of claim 7, further comprising an electrically insulating core, an electrically conductive housing bordering the core, and a feedthru wire extending through the core, wherein the filter assembly is coupled to at least one of the housing and core.

9. The EMI filtered feedthru of claim 8, wherein the filter assembly further includes a power trace and ground trace, wherein the power trace is in electrical communication with the feedthru wire and a power side of the capacitor and the ground trace is in electrical communication with a ground side of the capacitor and the housing.

10. The EMI filtered feedthru of claim 7, wherein the filter assembly further includes a power trace and a ground trace, and wherein the power trace is in electrical communication with a power side of the capacitor and a ground trace is in electrical communication with a ground side of the capacitor.

11. The EMI filtered feedthru of claim 7, wherein the capacitor further has a third capacitor layer adjacent and substantially parallel to the second capacitor layer such that the second capacitor layer is disposed between the first and third capacitor layers, the surface area of the third capacitor layer being less than the surface area of the second capacitor layer.

12. The EMI filtered feedthru of claim 11, wherein said first, second, and third capacitor layers together define a trapezoidal capacitor configuration.

13. An implantable pulse generator, comprising:
an EMI filtered feedthru including a filter assembly including a trapezoidal multi-layer thick film chip capacitor having a capacitance in the range of 1-5 nF, the capacitor having
a first capacitor layer, and
a second capacitor layer adjacent and substantially parallel to the first capacitor layer and having a surface area that is less than the surface area of the first capacitor layer; and
a body including a cavity in which the capacitor resides.

14. The implantable pulse generator of claim 13, further comprising an electrically insulating core, an electrically conductive housing bordering the core, and a feedthru wire extending through the core, wherein the filter assembly is coupled to at least one of the housing and core.

15. The implantable pulse generator of claim 14, wherein the filter assembly further includes a power trace and ground trace, wherein the power trace is in electrical communication with the feedthru wire and a power side of the capacitor and the ground trace is in electrical communication with a ground side of the capacitor and the housing.

16. The implantable pulse generator of claim 13, wherein the filter assembly further includes a power trace and a ground trace, and wherein the power trace is in electrical communication with a power side of the capacitor and a ground trace is in electrical communication with a ground side of the capacitor.

17. The implantable pulse generator of claim 13, further comprising:
a third capacitor layer adjacent and substantially parallel to the second capacitor layer such that the second capacitor layer is disposed between the first and third capacitor layers, the surface area of the third capacitor layer being less than the surface area of the second capacitor layer.

18. The implantable pulse generator of claim 17, wherein said first, second and third capacitor layers together define a trapezoidal capacitor configuration.

19. The EMI filtered feedthru of claim 7, wherein the filter assembly further includes additional capacitors and the body includes additional cavities, and wherein the additional capacitors reside in the additional cavities, and wherein the additional cavities are configured such that a separation distance at an inner edge of a neighboring capacitor is the same as a separation distance at an outer edge of the neighboring capacitor.

20. The implantable pulse generator of claim 13, wherein the filter assembly further includes additional capacitors and the body includes additional cavities, and wherein the additional capacitors reside in the additional cavities, and wherein the additional cavities are configured such that a separation distance at an inner edge of a neighboring capacitor is the same as a separation distance at an outer edge of the neighboring capacitor.

* * * * *